(12) United States Patent
Suzuki et al.

(10) Patent No.: US 8,758,266 B2
(45) Date of Patent: Jun. 24, 2014

(54) TREATMENT INSTRUMENT FOR ENDOSCOPE

(75) Inventors: Keita Suzuki, Tokyo (JP); Masatoshi Sato, Yokohama (JP); Takuo Yokota, Tokyo (JP); Shunsuke Motosugi, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/565,282

(22) Filed: Aug. 2, 2012

(65) Prior Publication Data

US 2013/0046338 A1   Feb. 21, 2013

Related U.S. Application Data

(63) Continuation of application No. PCT/JP2012/054776, filed on Feb. 27, 2012.

(30) Foreign Application Priority Data

Mar. 3, 2011   (JP) .................................. 2011-046408

(51) Int. Cl.
*A61B 10/06* (2006.01)
*A61B 17/29* (2006.01)
(52) U.S. Cl.
USPC ............................ 600/564; 606/174; 606/205
(58) Field of Classification Search
CPC ........................................... A61B 2017/00367
USPC .......... 606/167, 174, 205; 600/149, 564, 118, 600/130, 131, 138
See application file for complete search history.

(56) References Cited

U.S. PATENT DOCUMENTS

| 4,178,810 | A |   | 12/1979 | Takahashi |
|---|---|---|---|---|
| 5,009,661 | A | * | 4/1991 | Michelson ..................... 606/205 |
| 5,312,433 | A | * | 5/1994 | Boebel et al. .................. 606/205 |
| 5,683,413 | A |   | 11/1997 | Miyagi |
| 6,096,058 | A |   | 8/2000 | Boche |
| 7,828,808 | B2 | * | 11/2010 | Hinman et al. ............... 606/108 |

FOREIGN PATENT DOCUMENTS

| JP | A-7-299075 | 11/1995 |
|---|---|---|
| JP | A-8-38492 | 2/1996 |
| JP | A-10-290803 | 11/1998 |
| JP | A-2001-501126 | 1/2001 |
| JP | A-2010-167084 | 8/2010 |

OTHER PUBLICATIONS

Nov. 28, 2012 Search Report issued in European Patent Application No. 12752122.7.
Mar. 27, 2012 International Search Report issued in International Application No. PCT/JP2012/054776 (with translation).

* cited by examiner

*Primary Examiner* — Kathleen Holwerda
*Assistant Examiner* — Sarah W Aleman
(74) *Attorney, Agent, or Firm* — Oliff PLC

(57) ABSTRACT

A treatment tool for an endoscope includes a sheath member, a treatment part, an operating part body, an operating wire, a slider, and a force limiting part. When a predetermined force is applied to the force limiting part with advance and refraction of the slider, the force limiting part engages a wall surface of the insertion passage of the operating wire and fixes the slider by being compressed in an advance-and-retraction direction and expanding in a radial direction.

8 Claims, 10 Drawing Sheets

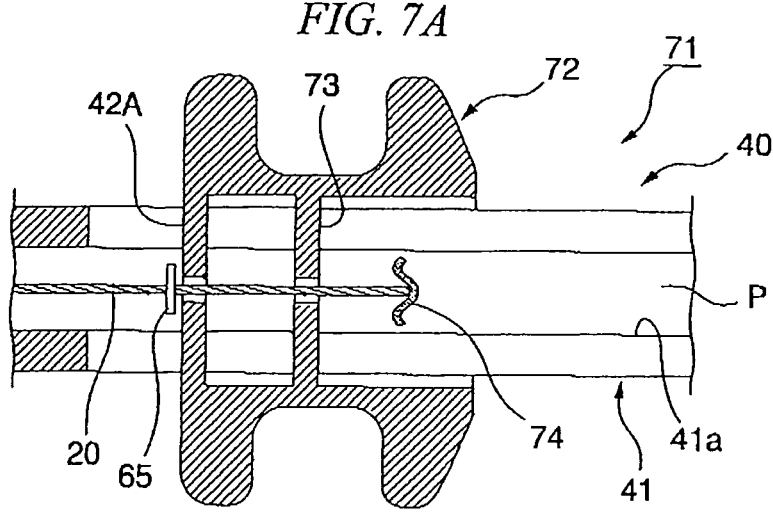
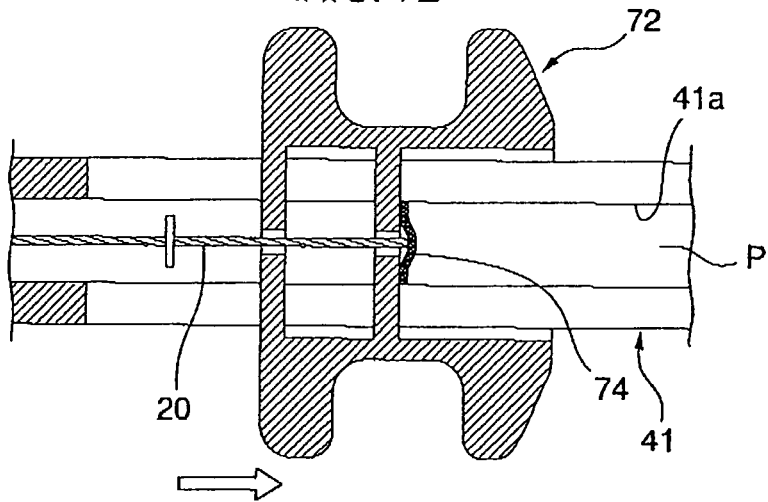
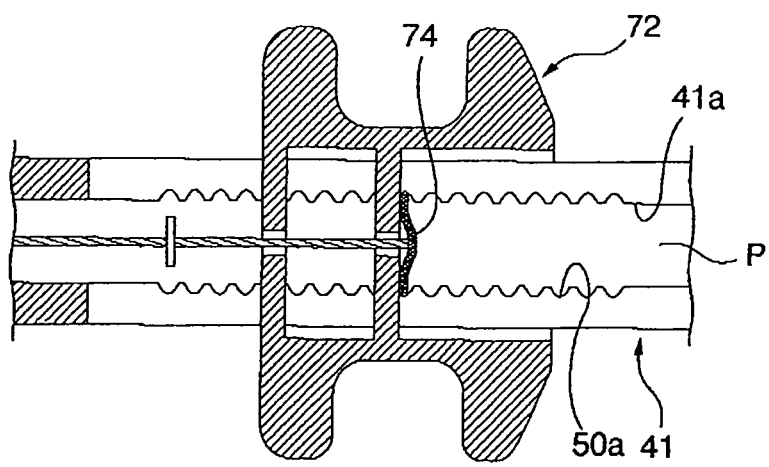

TREATMENT INSTRUMENT FOR ENDOSCOPE

This application is a Continuation of International Application No. PCT/JP2012/054776, filed on Feb. 27, 2012, claiming priority based on Japanese Patent Application No. 2011-046408, filed on Mar. 3, 2011. The contents of both the Japanese Patent Application and the PCT Application are incorporated herein by reference.

BACKGROUND ART

1. Field of the Invention

The present invention relates to a treatment tool for an endoscope that is used after being endoscopically inserted into a body cavity.

2. Background Art

Conventionally, as treatment tools for an endoscope (hereinafter simply referred to as "treatment tools") that have a flexible sheath and is used after being endoscopically inserted into a body cavity, forceps having a pair of forceps members that are relatively pivotally supported by a pivot shaft are known.

The pair of forceps members is connected with an operating part on the hand side by an operating wire. The pair of forceps members can be relatively pivoted around the pivot shaft, and opened and closed by advancing and retracting the operating wire in an axis direction via the operating part.

In such forceps, if the operating wire continues being retracted even after the pair of forceps members is closed, a larger force acts on the forceps members.

Japanese Unexamined Patent Application, First Publication No. 10-290803 suggests a treatment tool including display unit that detects and displays a force that acts on a treatment part, such as forceps members, with the operation of an operating slider that advances retracts the operating wire, depending on the deflection amount of an elastic body. An operator can perceive the force that acts on the treatment part using the display unit, and can adjust the operation amount of the operating slider, to thereby regulate the force.

SUMMARY OF THE INVENTION

The treatment tool for an endoscope related to a first aspect of the present invention includes a sheath member which has a distal end and a proximal end; a treatment part which is provided at the distal end of the sheath member; an operating part body which is provided at the proximal end of the sheath member to operate the treatment part; an operating wire which is connected to the treatment part in order to transmit a driving force to the treatment part and is arranged through an insertion passage extending from the sheath member to the operating part body; a slider which is provided in the operating part body, and causes the operating wire to advance and retract and causes the treatment part to drive by sliding with respect to the operating part body; and a force limiting part which connects the operating wire and the slider and made of an elastic body. When a predetermined force is applied to the force limiting part with advance and retraction of the slider, the force limiting part engages a wall surface of the insertion passage of the operating wire and fixes the slider by being compressed in an advance-and-retraction direction and expanding in a radial direction.

According to a second aspect, in the first aspect, the insertion passage may be formed within the operating part body, and the force limiting part may be located within the operating part body.

Additionally, according to a third aspect, in the first aspect, the force limiting part may be attached to a proximal end portion of the operating wire, and the force limiting part may be pressed against the slider and is deformed when being compressed in the advance-and-retraction direction.

Moreover, according to a fourth aspect, in the first aspect, the operating wire may have a first region connected to the treatment part and a second region connected to the slider, and the force limiting part may connect the first region and the second region.

According to a fifth aspect, in any one of the second to fourth aspects, friction may be generated between the elastic body and the operating part body by a deformation of the elastic body, and the elastic body may be engaged with the operating part body by the friction.

According to a sixth aspect, in any one of the first to fifth aspects, a corrugated surfaceconcave-convex surface which engages with that meshes with the elastic body that has expanded in the radial direction may be formed in the wall surface.

According to a seventh aspect, in any one of the first to sixth aspects, the treatment part may have a pair of gripping forceps, and a gripping forces of the pair of gripping forceps may be limited to a predetermined value or lower by the force limiting part.

BRIEF DESCRIPTION OF THE DRAWINGS

FIG. 7A is a view showing an operating part of a treatment tool for an endoscope of a third embodiment of the present invention.

FIG. 7B is a view showing the same operating part when the third embodiment of the present invention is used.

FIG. 8 is a view showing the operating part when the treatment tool for an endoscope in the modified example of the present embodiment is used.

PREFERRED EMBODIMENTS

Figure 1:
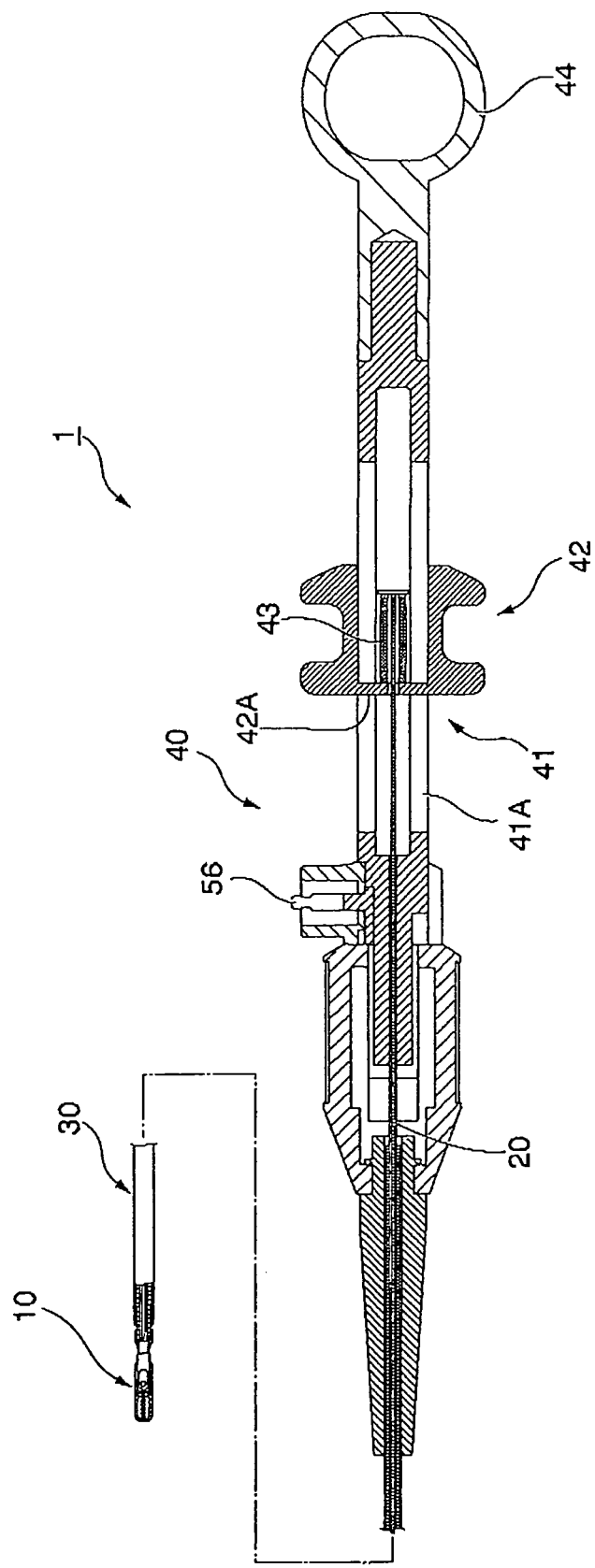
FIG. 1 is an overall view showing a treatment tool for an endoscope of a first embodiment of the present invention in a partial cross-section.

A treatment tool for an endoscope of a first embodiment of the present invention will be described with reference to FIGS. 1 to 5B. As shown in FIG. 1, a treatment tool 1, which is the treatment tool for an endoscope of the present embodiment, includes a coiled sheath (sheath member) 31 having a distal, end and a proximal end, a treatment part 10 provided at the distal end of the coiled sheath 31 to perform a treatment on tissues within a body cavity, an operating part 40 provided at the proximal end of the sheath member 31 and having an operating part body 41 for operating the treatment part 10, an operating wire 20 connected to the treatment part 10, a long insertion part 30 inserted into the body cavity, a slider 42, and an elastic body (force limiting member) 43.

Figure 2:
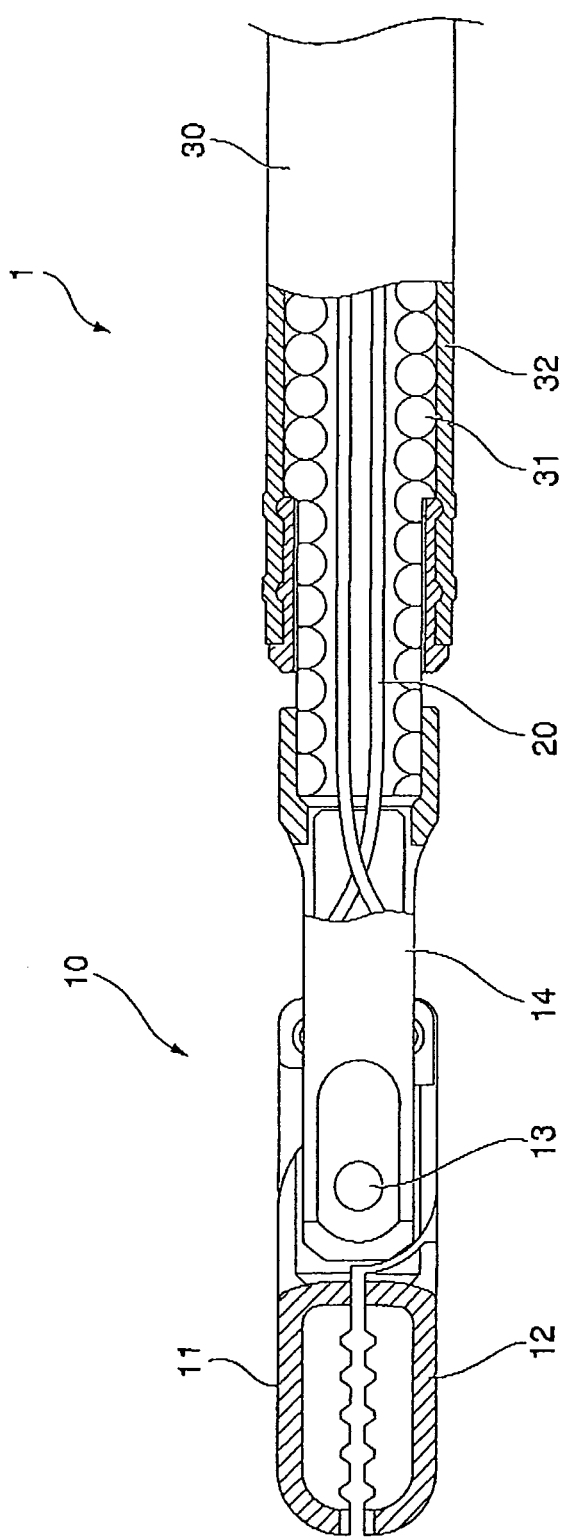
FIG. 2 is an enlarged view showing a distal end portion of the treatment tool for an endoscope of the first embodiment of the present invention in a partial cross-section.

FIG. 2 is an enlarged view showing a distal end portion of the treatment tool 1 including the treatment part 10 in a partial cross-section. The treatment part 10 is adapted such that a pair of forceps members of a first forceps member 11 and a second forceps member 12 is relatively pivotally (rotatably) coupled and supported by a pivot shaft 13 supported by a cover member 14. The operating wire 20 is connected closer to the proximal end side than the pivot shaft 13 of the respective forceps members 11 and 12, and extends to the operating part 40 through the inside of the insertion part 30. The operating wire 20 is connected to the treatment part 10 in order to transmit a driving force, and is arranged through an insertion passage P extending from the coiled sheath 31 to the operating part body 41.

The insertion part 30 is formed in a long tubular shape through which the operating wire 20 is inserted, and has the coiled sheath 31, and an insulating tube sheath 32 that covers the outside of the coiled sheath 31. A cover member 14 is fixed to the distal end of the insertion part 30, and the pivot shaft 13 is supported so as not to move relative to the insertion part 30. The proximal end side of the insertion part 30 is attached to the operating part 40.

As shown in FIG. 1, the operating part 40 includes the operating part body 41 through which the operating wire 20 is inserted, and the slider (slide member) 42 provided at the operating part body 41 and attached so as to be able to advance and retract with respect to the operating part body 41. The slider 42 slides with respect to the operating part body 41, and advances and retracts the operating wire 20 to move the treatment part 10.

The operating part body 41 is formed of resin or the like, and has therein a space through which the operating wire 20 is inserted. The operating part body 41 is formed with a slot 41A that extends in a longitudinal direction and communicates with the insertion passage P. This insertion passage P is formed to the inside of the operating part body 41. A finger hooking handle 44 is provided on the proximal end side of the operating part body 41.

The slider 42 is formed in a substantially tubular shape using resin or the like. The internal diameter of the slider 42 is slightly greater than the external diameter of the operating part body 41. A locking portion 42A arranged within the slot 41A and in the insertion passage P is provided on the distal end side of the slider 42. Accordingly, as the locking portion 42A moves along the slot 41A, the slider 42 is slidable so as to move relative to the operating part body 41.

Figure 3A:
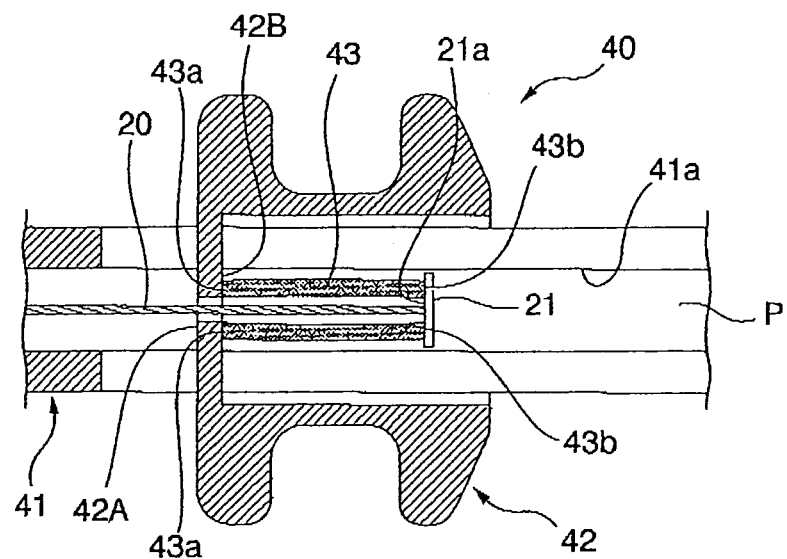
FIG. 3A is a view showing an operating part of the treatment tool for an endoscope of the first embodiment of the present invention.

As shown in FIG. 3A, the proximal end side of the operating wire 20 extends closer to the proximal end side than the locking portion 42A through a hole formed in the locking portion 42A. A plate-shaped connecting member 21 is fixed to a proximal end portion of the operating wire 20. An elastic body 43 is located within the operating part body 41, and the connecting member 21 and the locking portion 42A are connected by the tubular elastic body 43. The length direction of the elastic body 43 and the length direction of the operating wire 20 are the same. Additionally, this elastic body 43 is deformed by a force (a second force) applied when the slider 42 is retracted, and fixes the slider 42 to the operating part body 41. A distal end 43a side of the elastic body 43 is fixed to a face 42B of the locking portion 42A of on the proximal end side, and a proximal end 43b side of the elastic body 43 is fixed to a face 21a of the connecting member 21 on the distal end side. The operating wire 20 is inserted through an inner cavity of the elastic body 43. That is, since the operating wire 20 and the slider 42 are connected via the elastic body 43, the operating wire 20 can be advanced and retracted in an axis direction via the slider 42.

As the material of the elastic body 43, a material having a high coefficient of friction of an outer peripheral surface is preferable, for example, rubber, elastomer, or the like can be used.

Additionally, as shown in FIG. 1, the operating part 40 is provided with a plug 56 for applying a current to the treatment part 10. If the plug 56 is connected to a high-frequency power source (not shown), a high-frequency current can be supplied to the treatment part 10 via the operating wire 20.

The operation when the treatment tool 1 configured as described above is used will be described.

First, an endoscope (not shown) is shown into the body of a patient, and the distal end of the endoscope is advanced to the vicinity of tissues within a body cavity that is a target to be treated.

The user causes the slider 42 to slide toward the proximal end side of the operating part body 41 (hereinafter, the operation in this direction is referred to as "retraction"). Thereby, since the pair of forceps members 11 and 12 is brought into a closed state, the treatment part 10 and the insertion part 30 are inserted into a forceps channel of the endoscope in this state. Then, the treatment part 10 is made to protrude from the distal end of the forceps channel.

The user operates the operating part 40 to perform a treatment on a target tissue using the treatment part 10 while observing the target tissue using the endoscope.

When the pair of forceps members 11 and 12, the slider 42 is made to slide to the distal end side of the operating part body 41 (hereinafter the operation in this direction is referred to as "advance"). This advances the operating wire 20 connected to the slider 42. As described above, since the pivot shaft 13 is supported by the cover member 14 attached to the insertion part 30, the first forceps member 11 and the second forceps member 12 are pivoted, respectively, around the pivot shaft 13 fixed to the insertion part 30, and the treatment part 10 opens.

If an object is located between the first forceps member 11 and the second forceps member 12 and a user retreats the slider 42, the object is sandwiched and gripped between the first forceps member 11 and the second forceps member 12.

Although the slider 42 can be slightly retracted even after the object is sandwiched, if the object is compressed to a certain degree, the slider 42 cannot be further retracted. If the slider 42 is pulled so as to be retracted in this state, the pulling force is transmitted to the pair of forceps members 11 and 12 via the operating wire 20, and the force (first force) that acts on (is applied to) the object increases.

Figure 3B:
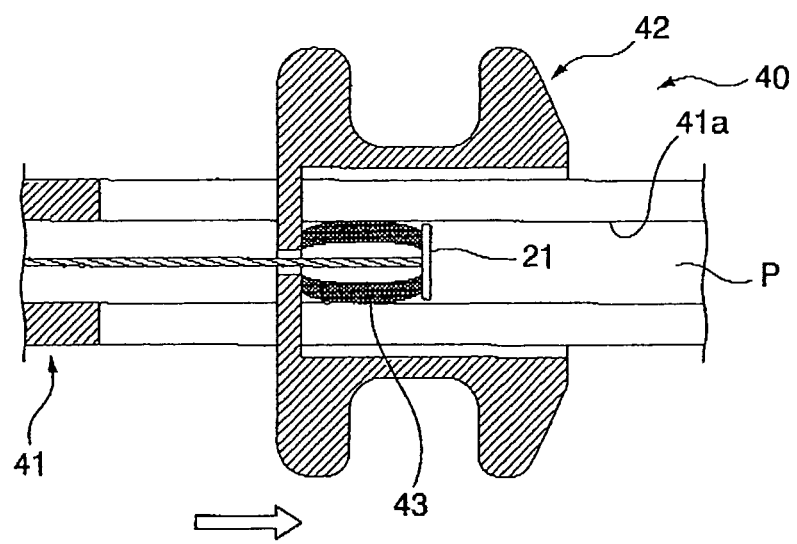
FIG. 3B is a view showing the operating part when the treatment tool for an endoscope of the first embodiment of the present invention is used.

If the force that pulls the slider 42 is increased to such magnitude that the tubular elastic body 43 can be compressed in the axis direction, the slider 42 retreats with respect to the operating part body 41 while compressing the elastic body 43 as shown in FIG. 3B.

If the elastic body 43 is compressed in the axis direction, the dimension of the elastic body 43 in the radial direction (vertical direction in the drawing) increases and deforms. Eventually, the elastic body 43 comes into contact with the wall surface 41a of the insertion passage P of the operating part body 41, and friction is generated between the elastic body 43 and the wall surface 41a of the insertion passage P. The elastic body 43 is engaged with the operating part body 41 (wall surface 41a of the insertion passage P) by this friction. The slider 42 is held so as to be substantially non-slidable with respect to the operating part body 41 by this frictional force, and the force that acts on an object from the treatment part 10 does not increase any more, and is limited to a predetermined value or less.

If a high-frequency current is supplied to the treatment part 10 from the plug 56 in a state where an object is gripped, the gripped object is cauterized.

According to the treatment tool 1 of the present embodiment, if the force that pulls the slider 42 becomes a predetermined magnitude, the elastic body 43 that connects the slider 42 and the operating wire 20 is compressed and deformed in the axis direction. If the elastic body 43 is compressed by a predetermined amount and brought into contact with the operating part body 41, the slider 42 that advances and retracts the operating wire 20 is fixed to the operating part body 41, and the force that acts on an object gripped by the pair of forceps members 11 and 12 is limited to a predetermined value or less.

Accordingly, the force to act can be easily kept at a certain value or less while preventing superfluous force from acting on the gripped object, simply by performing the same operation as the conventionally treatment tool that pulls the slider so as to be retracted. As a result, a treatment can be more exactly performed on an object by easy operation.

Additionally, the slider 42 is fixed to the operating part body 41 not on the basis of the movement distance of the slider but on the basis of the force that acts on the slider. Thereby, the magnitude of the maximum force that acts on the treatment part 10 does not change even if the initial position of the slider before operation changes, for example, due to the insertion part 30 meandering within the forceps channel of the endoscope. Accordingly, the maximum force in the treatment part can be a predetermined magnitude, without being influenced by usage environment The timing at which the slider 42 is fixed to the operating part body 41 can be appropriately regulated by replacing the elastic body 43 with those having different external diameters, materials, or the like, and thereby the maximum force that acts on an object can be adjusted.

In the present embodiment, the slider 42 is fixed to the operating part body 41 by the friction between the elastic body 43 and the wall surface 41a of the insertion passage P, but the present invention is not limited to this configuration.

Additionally, although an example in which the elastic body is tubular is described in the present embodiment, the aspect of the elastic body is not limited to this configuration.

Figure 4A:
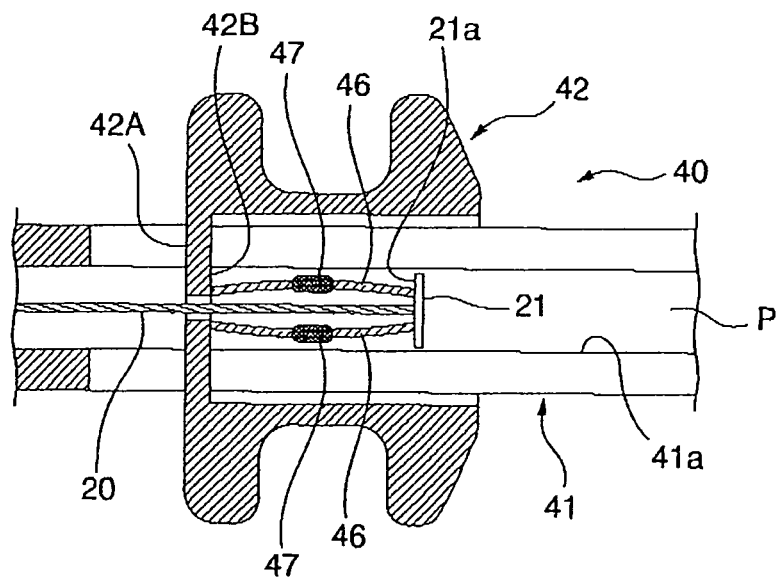
FIG. 4A is a view showing an operating part of a treatment tool for an endoscope of a modified example of the present embodiment.
Figure 4B:
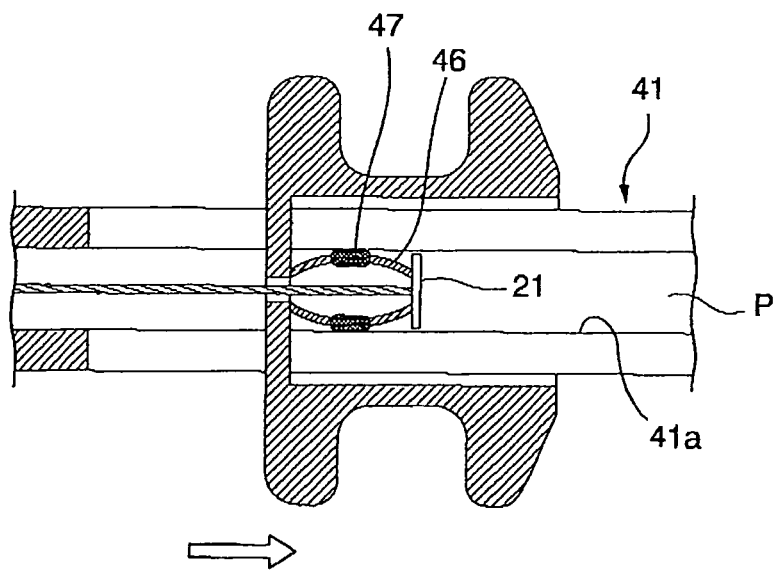
FIG. 4B is a view showing the operating part when the treatment tool for an endoscope of the modified example of the present embodiment is used.

A modified example of the present embodiment is shown in FIGS. 4A and 4B. In this modified example, as shown in FIG. 4A, a pair of plate springs 46 formed of metal or the like is used as an elastic body. The pair of plate springs 46 connects the face 42B of the locking portion 42A on the proximal end side and the face 21a of the connecting member 21 on the distal end side at positions that face each other with the operating wire 20 therebetween. A longitudinal central portion of each plate spring 46 is covered with a covering member 47 made of silicone rubber, nitrile rubber, or the like with a high coefficient of friction.

In this modified example, if the plate springs 46 are compressed, as shown in FIG. 4B, the covering members 47 come into contact with the wall surface 41a of the insertion passage P, and the covering members 47 and the operating part body 41 are engaged with each other by the friction therebetween. Even in a case where the coefficient of friction of the elastic body itself is not high in this way, it is possible to fix the slider 42 to the operating part body 41. Additionally, in a case where the plate springs are formed of metal, since the plate springs generally have a smaller variation in elastic modulus than elastic bodies, such as rubber, high-precision force control is possible.

In addition, there is no particularly limitation on the number of the plate spring 43, and three or more plate springs may be arranged at regular intervals around the axis of the operating wire.

Figure 5A:
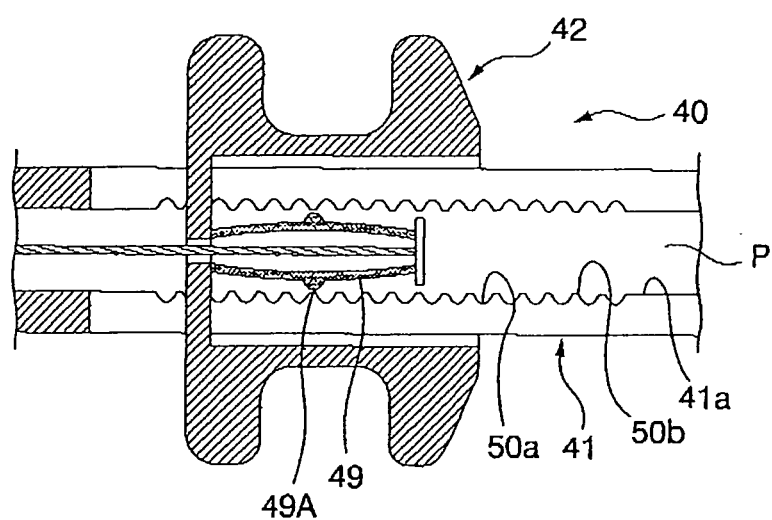
FIG. 5A is a view showing an operating part of a treatment tool for an endoscope of another modified example of the present embodiment.
Figure 5B:
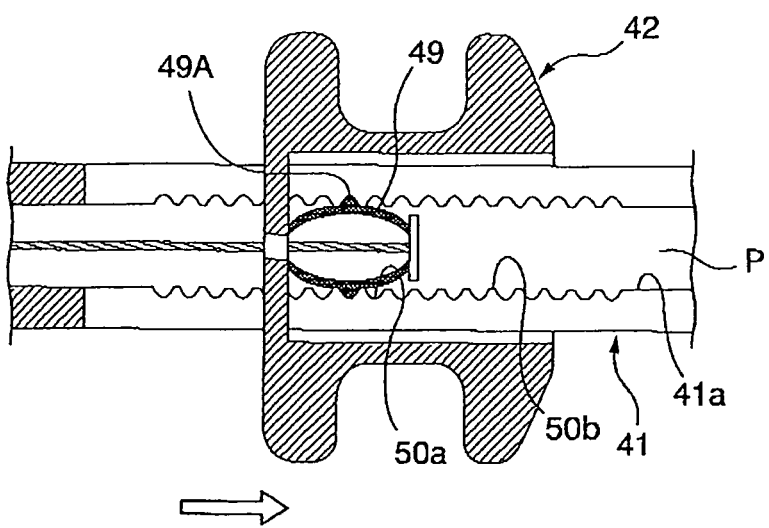
FIG. 5B is a view showing the operating part when another modified example of the present embodiment is used.

Another modified example of the present embodiment is shown in FIGS. 5A and 5B. In this modified example, as shown in FIG. 5A, at least one engaging projection 49A is formed on the surfaces of a pair of metallic springs (elastic bodies) 49 that face the wall surface 41a of the insertion passage P. The wall surface 41a of the insertion passage P is formed with a concave-convex surface that meshes with the metallic springs 49 that have expanded in the radial direction. This concave-convex surface has a plurality of concave portions 50a and a plurality of convex portions 50b, and the plurality of concave portions 50a and the plurality of convex portions 50b are formed along the longitudinal direction of the operating part body 41. This enables the engaging projection 49A of the metallic springs 49 to engage one of the plurality of concave portions 50a.

In this modified example, if the elastic bodies 49 are compressed, as shown in FIG. 5B, the engaging projection 49A engages the concave portion 50a. The slider 42 is fixed to the operating part body 41 by this mechanical engagement. Therefore, the slider can be more reliably fixed to the operating part body.

In addition, such mechanical engagement can also be applied to the configuration using the tubular elastic bodies shown in FIGS. 3A and 3B.

Next, a second embodiment of the present invention will be described with reference to FIGS. 6A and 6B. A treatment tool 61 of the present embodiment is different from the treatment tool 1 of the first embodiment in the arrangement aspect of a force regulating member. In addition, in the following description, components common to those of the treatment tools of the respective embodiments already described will be designated by the same reference numerals, and duplicate description will be omitted.

Figure 6A:
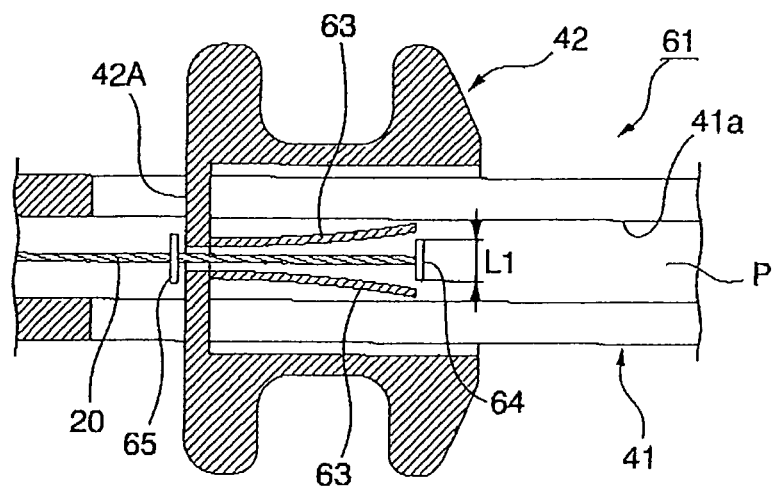
FIG. 6A is a view showing an operating part of a treatment tool for an endoscope of a second embodiment of the present invention.
Figure 6B:
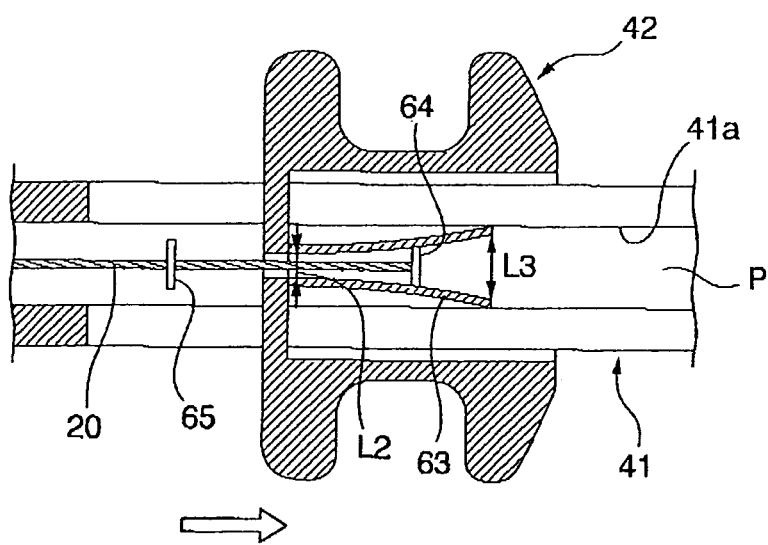
FIG. 6B is a view showing the operating part when the second embodiment of the present invention is used.

FIGS. 6A and 6B are enlarged cross-sectional views showing the surroundings of the slider 42 of the treatment tool 61. As shown in FIG. 6A, a pair of lock members (force limiting members) 63 having certain rigidity is connected to the surface of the locking portion 42A on the proximal end side. The pair of lock members 63 is arranged at positions that face each other with the operating wire 20 therebetween. Each lock member 63 is slightly curved so as to approach the wall surface 41a of the insertion passage P toward the proximal end. As the lock members 63, metallic elastic bodies, such as the above-described plate springs 46, can be favorably used.

Although an expansion member 64 of the same material and shape as the connecting member 21 is attached to the proximal ends of the operating wire 20, the expansion member is not connected with the lock members 63, and the operating wire 20 and the slider 42 are not directly connected. The dimension L1 of the expansion member 64 in the direction in which the lock members 63 face each other is greater than the distance L2 in a region connected to the locking portion 42A and smaller than the distance L3 at the proximal end, in the distance between the pair of lock members 63.

Additionally, in the operating wire 20, an abutting plate 65 capable of abutting the locking portion 42A is fixed to a predetermined position closer to the distal end side than the slider 42.

Although the basic operation of the treatment tool 61 is almost the same as that of the treatment tool 1, different points will be described below.

If the slider 42 is advanced, the face of the locking portion 42A on the distal end side abuts on the abutting plate 65, and the abutting plate 65 is pushed and the operating wire 20 is advanced, thereby the treatment part 10 (not shown) opens.

If the slider 42 is retracted, as shown in FIG. 6B, the expansion member 64 at the based ends of the operating wire 20 enters between the lock members 63 from the proximal end side of the pair of lock members 63 and engages the lock members 63. This enables the operating wire 20 to be retracted.

If the force that pulls the slider 42 increases after the treatment part 10 is closed, the expansion member 64 tends to move closer to the distal end side between the lock members 63. This pushes apart the pair of lock members 63 to thereby cause the proximal end of each lock member 63 to approach the wall surface 41a of the insertion passage P. If the force that pulls the slider 42 reaches a predetermined magnitude, the proximal end of each lock member 63 comes into contact with the wall surface 41a of the insertion passage P, and is locked to the operating part body 41. As a result, the slider 42 is fixed to the operating part body 41.

Even in the treatment tool 61 of the present embodiment, the gripping force that acts on an object gripped by the treatment part can be easily limited to a predetermined value simply by performing the same operation as the conventionally treatment tool, similarly to the treatment tool of the first embodiment.

Next, a third embodiment of the present invention will be described with reference to FIGS. 7A to 9B. A treatment tool 71 of the present embodiment is different from the treatment tool 1 of the first embodiment in the arrangement aspect of a force regulating member.

FIGS. 7A and 7B are enlarged cross-sectional views showing the surroundings of a slider 72 of the treatment tool 71. As shown in FIG. 7A, a second locking portion 73 of the same shape as the locking portion 42A is provided on the proximal end side of the locking portion 42A in the slider 72.

An elastic body (force limiting member) 74 made of metal or the like is fixed to the proximal end portion of the operating wire 20. The elastic body 74 is curved in a thickness direction (direction parallel to the axis of the operating wire 20) as shown in FIG. 7A, and is formed into a shape such that the elastic body does not contact the wall surface 41a of the insertion passage P in a state where external force does not act.

If the force that pulls the slider 72 increases after the treatment part is closed when the treatment tool 71 is used, the elastic body 74 is compressed in the advance-and-retraction direction, and the second locking portion 73 and the elastic body 74 abuts against each other first. Thereafter, by pressing the elastic body against the second locking portion 73, the elastic body deforms so as to become flat in the thickness direction. As a result, as shown in FIG. 7B, the end portions of the elastic body 74 in the planar direction (direction orthogonal to the thickness direction) come into contact with the wall surface 41a of the insertion passage P, and engages the wall surface by friction, and the slider 72 is fixed to the operating part body 41.

Even in the treatment tool 71 of the present embodiment, the force that acts on an object gripped by the treatment part can be easily limited to a predetermined value or less simply by performing the same operation as the conventionally treatment tool, similarly to the treatment tool of the first embodiment. Additionally, since the limitation of the force is possible simply by attaching a predetermined elastic body to the proximal end of the operating wire, the same effects as those of the above-described respective embodiments can be obtained while reducing the number of parts and simplifying the configuration.

In the present embodiment, similarly to a modified example shown in FIG. 8, the above-described concave portions 50a may be provided in the operating part body 41, and the engagement between the elastic body 74 and the operating part body 41 may be made more reliable.

Additionally, the shape of the elastic body is not limited to the shape like the elastic body 74. A modified example including a different elastic body is shown in FIGS. 9A and 9B.

Figure 9A:
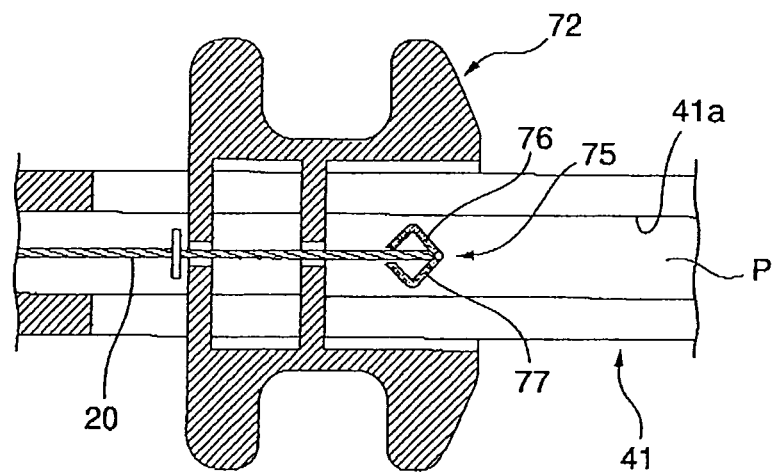
FIG. 9A is a view showing an operating part of a treatment tool for an endoscope of a modified example of the present embodiment.
Figure 9B:
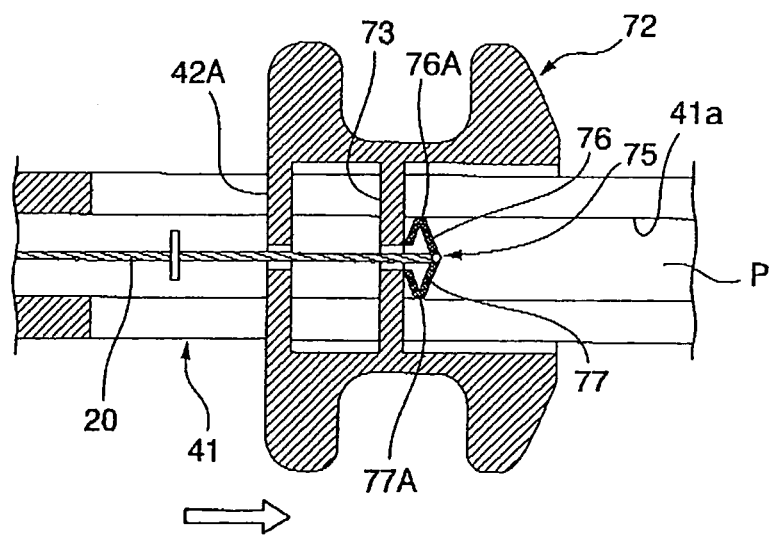
FIG. 9B is a view showing the same operating part when the modified example of the present embodiment is used.

As shown in FIG. 9A, an elastic body 75 connected to the proximal end portion of the operating wire 20 has a pair of arm portions 76 and 77 made of metallic springs that are bent so as to become convex toward the wall surface 41a of the insertion passage P of the operating part body 41. The arm portions 76 and 77 are arranged so as to face each other with the operating wire 20 therebetween, and are formed in the shape of a so-called pantograph as the whole elastic body 75.

In this modified example, convex portions 76A and 77A of the respective arm portion 76 and 77 that come into contact with the wall surface 41a of the insertion passage P are respectively supported by a region closer to the distal end side than the convex portions 76A and 77A and a region closer to the proximal end side than the convex portions 76A and 77A. Therefore, the convex portions come into contact with the wall surface 41a of the insertion passage P with a larger deployment force than the elastic body 74. Accordingly, the slider 72 and the operating part body 41 can be more reliably fixed.

Moreover, an example in which the slider includes the second locking portion 73 is described in the present embodiment. However, instead of this, the elastic body 74, 75 or the like may be made to abut against the locking portion 42A without including the second locking portion 73.

Next, a fourth embodiment of the present invention will be described with reference to FIGS. 10A to 11. A treatment tool 81 of the present embodiment is different from the treatment tool 1 of the first embodiment in the arrangement aspect of a force regulating member.

Figure 10A:
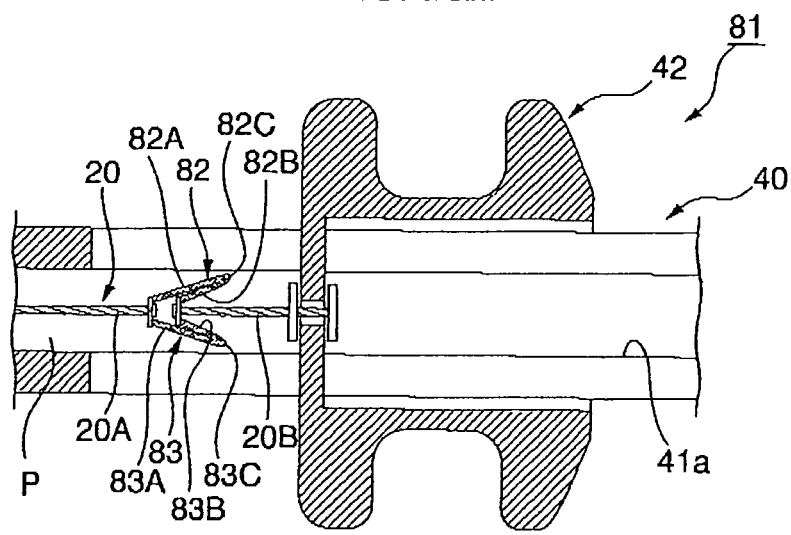
FIG. 10A is a view showing an operating part of the treatment tool for an endoscope of a fourth embodiment of the present invention.
Figure 10B:
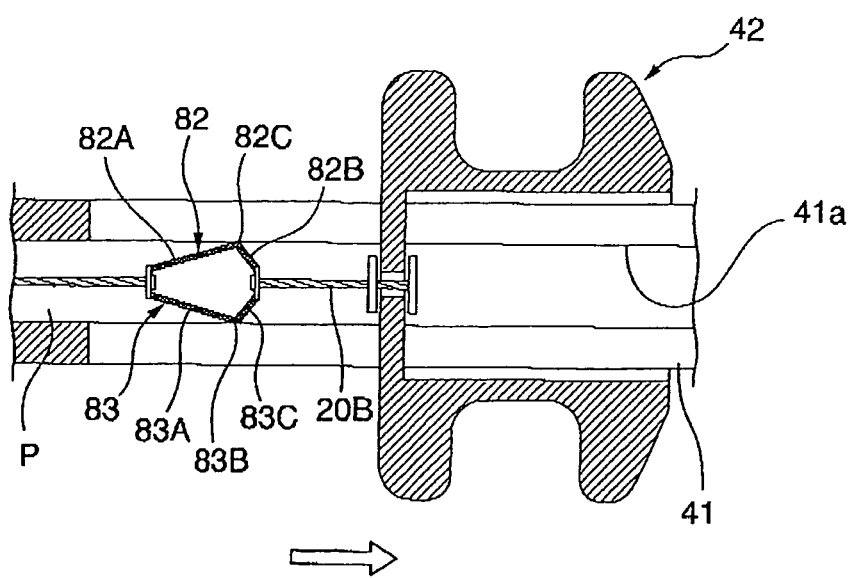
FIG. 10B is a view showing the same operating part when the fourth embodiment of the present invention is used.

FIGS. 10A and 10B are enlarged cross-sectional views showing the surroundings of the slider 42 of the treatment tool 81. As shown in FIG. 10A, the proximal end portion of the operating wire 20 is directly connected and fixed to the slider 42. The operating wire 20 is divided into a first region 20A on the distal end side and a second region 20B on the proximal end side, on the distal end side of the slider 42. A pair of bent springs (elastic bodies, force limiting members) 82 and 83 is arranged between the first region 20A and the second region 20B to connect the first region 20A and the second region 20B.

The bent springs 82 and 83 have first arm portions 82A and 83A connected to the first region 20A and second arm portions 82B and 83B connected to the second region 20B, respectively. Bent points 82C and 83C between the first arm portions and the second arm portions are located closer to the proximal end side than connecting points between the second region 20B and the second arm portions 82B and 83B in an initial state.

If the force that pulls the slider 42 increases after the treatment part is closed when the treatment tool 81 is used, as shown in FIG. 10B, the connecting points between the second region 20B and the second arm portions 82B and 83B move to the proximal end side. As a result, the respective bent springs 82 and 83 are deployed, the bent points 82C and 83C engage the wall surface 41a of the insertion passage P by friction, and the slider 42 is fixed to the operating part body 41.

Even in the treatment tool 81 of the present embodiment, the force that acts on an object gripped by the treatment part can be easily limited to a predetermined value simply by performing the same operation as the conventionally treatment tool, similarly to the treatment tool of the first embodiment Additionally, since the proximal end portion of the operating wire can be directly fixable to the slider similarly to the conventionally treatment tool, a feeling of operation can be brought close to that of the conventionally treatment tool.

Additionally, since the bent points of the respective bent springs are supported by the first arm portions and the second arm portions, the slider can be more reliably fixed.

Moreover, since the bent springs are arranged at positions spaced apart from the slider, the inside of the slider does not become complicated, and a treatment tool with a simple structure can be provided.

Figure 11:
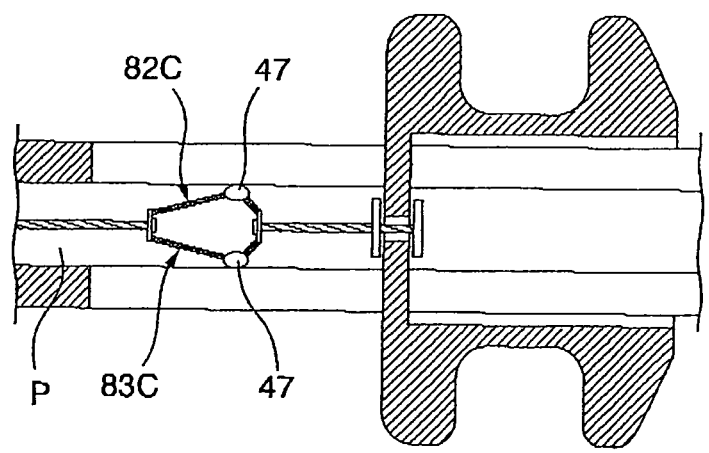
FIG. 11 is a view showing the operating part when the treatment tool for an endoscope in the modified example of the present embodiment is used.

In the treatment tool of the present embodiment, the covering members 47 may be attached to the bent points 82C and 83C similarly to a modified example shown in FIG. 11. If this configuration is adopted, the slider can be still more reliably fixed.

Although the respective embodiments of the present invention have been described hitherto, the technical scope of the present invention is not limited to the above respective embodiments, but combinations of constituent elements of the respective embodiments can be changed, various alternations can be made to the respective constituent elements, or omissions can be made, without departing from the concept of the present invention.

For example, the structure of the treatment tool of the present invention can also be applied to a treatment tool that does not apply a current to the treatment part. In this case, the plug may not be provided.

All the constituent elements described in the above respective embodiments and modified examples can be carried out by appropriately replacing or omitting combinations within the scope of the technical idea of the present invention.

Moreover, although the preferable embodiments of the present present invention have been described, the present present invention is not limited to these embodiments. Additions, omissions, substitutions, and other modified examples can be made without departing from the concept of the present present invention. Accordingly, the present present invention is not to be considered as being limited by the foregoing description, and is only limited by the scope of the appended claims.

The invention claimed is:

1. A treatment tool for an endoscope comprising:
    a sheath member which is flexible, and has a distal end and a proximal end;
    a treatment part which is provided at the distal end of the sheath member;
    an operating part body which is provided at the proximal end of the sheath member to operate the treatment part;
    an operating wire which is connected to the treatment part in order to transmit a driving force to the treatment part, the operating wire being disposed in an insertion passage that extends through the sheath member and the operating part body;
    a slider which is provided in the operating part body, causes the operating wire to advance and retract, and causes the treatment part to drive by sliding with respect to the operating part body; and
    a force limiting part, which connects the operating wire and the slider, located within the insertion passage, the force limiting part being made of an elastic body with an original shape, the force limiting part being compressed in an advance-and-retraction direction and expanding in a radial direction, and when a predetermined force is applied to the force limiting part with retraction of the slider, the force limiting part contacts a wall surface of the insertion passage such that frictional engagement of the force limiting part limits movement of the slider to the predetermined force, and wherein the force limiting part is returned to the original shape when the predetermined force is no longer applied.

2. The treatment tool for an endoscope according to claim 1,
    wherein the force limiting part is attached to a proximal end portion of the operating wire, and the force limiting part is pressed against the slider.

3. The treatment tool for an endoscope according to claim 1, wherein:
    the operating wire has a first region connected to the treatment part and a second region connected to the slider, and
    the force limiting part connects the first region and the second region.

4. The treatment tool for an endoscope according to claim 1,
    wherein the elastic body is engaged with the operating part body by a friction which is generated by a deforming of the elastic body.

5. The treatment tool for an endoscope according to claim 1,
    wherein a concave-convex surface which engages with the elastic body that has expanded in the radial direction is formed in the wall surface.

6. The treatment tool for an endoscope according to claim 1,
    wherein the treatment part has a pair of gripping forcepts, and
    a gripping force of the pair of gripping forceps is limited to a predetermined value by the force limiting part.

7. The treatment tool for an endoscope according to claim 2,
    wherein friction is generated between the elastic body and the operating part body by a deformating of the elastic body, and the elastic body is engaged with the operating part body by the friction.

8. The treatment tool for an endoscope according to claim 3,
wherein friction is generated between the elastic body and the operating part body by a deformation of the elastic body, and
the elastic body is engaged with the operating part body by the friction.

* * * * *